United States Patent
Barry et al.

(10) Patent No.: US 9,521,744 B2
(45) Date of Patent: Dec. 13, 2016

(54) FILTERED FEEDTHROUGH ASSEMBLY FOR IMPLANTABLE MEDICAL ELECTRONIC DEVICES

(71) Applicant: Cardiac Pacemakers, Inc., St. Paul, MN (US)

(72) Inventors: Patrick J. Barry, North St. Paul, MN (US); Randy White, Blaine, MN (US); Troy A. Giese, Blaine, MN (US); James E. Blood, Shoreview, MN (US); Michael J. Lyden, Shoreview, MN (US); Robert M. Mohn, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/628,119

(22) Filed: Feb. 20, 2015

(65) Prior Publication Data

US 2015/0245468 A1 Aug. 27, 2015

Related U.S. Application Data

(60) Provisional application No. 61/943,130, filed on Feb. 21, 2014.

(51) Int. Cl.
*A61N 1/08* (2006.01)
*H05K 1/02* (2006.01)
(Continued)

(52) U.S. Cl.
CPC ............ *H05K 1/0231* (2013.01); *A61N 1/08* (2013.01); *A61N 1/3754* (2013.01); *H05K 1/115* (2013.01);
(Continued)

(58) Field of Classification Search
CPC .................................................... A61N 1/3754
(Continued)

(56) References Cited

U.S. PATENT DOCUMENTS

| 4,726,790 A | 2/1988 | Hadjis |
| 4,729,743 A | 3/1988 | Farrar et al. |

(Continued)

FOREIGN PATENT DOCUMENTS

WO   WO-2015127319 A1   8/2015

OTHER PUBLICATIONS

International Search Report and Written Opinion issued in PCT/US2015/016975, mailed May 8, 2015, 9 pages.

*Primary Examiner* — Hung V Ngo
(74) *Attorney, Agent, or Firm* — Schwegman Lundberg & Woessner, P.A.

(57) ABSTRACT

A filtered feedthrough assembly for an implantable medical device includes a ferrule, an electrical insulator coupled to the ferrule by a connection element, a plurality of feedthrough conductors extending through the electrical insulator, a printed circuit board (PCB), and a plurality of capacitors. The PCB is coupled to the ferrule or the electrical insulator, and includes one or more ground layers and a plurality of vias. The connection element is electrically coupled to the ground layer through the vias. The capacitor has a ground terminal electrically coupled to the ground layer through at least one of the vias, and a conductor terminal electrically coupled to the feedthrough conductor.

19 Claims, 4 Drawing Sheets

(51) Int. Cl.
*H05K 1/11* (2006.01)
*H05K 1/18* (2006.01)
*H05K 3/10* (2006.01)
*H05K 3/32* (2006.01)
*A61N 1/375* (2006.01)

(52) U.S. Cl.
CPC ............... *H05K 1/181* (2013.01); *H05K 3/10* (2013.01); *H05K 3/32* (2013.01); *A61N 2001/086* (2013.01); *H05K 2201/10015* (2013.01); *Y10T 29/49139* (2015.01)

(58) Field of Classification Search
USPC ................................................ 174/360, 361
See application file for complete search history.

(56) References Cited

U.S. PATENT DOCUMENTS

| | | | |
|---|---|---|---|
| 4,729,752 A | | 3/1988 | Dawson et al. |
| 4,781,264 A | | 11/1988 | Matsuzaki et al. |
| 4,952,896 A | * | 8/1990 | Dawson, Jr. ....... H01R 13/7197 333/182 |
| 5,333,095 A | * | 7/1994 | Stevenson ............ A61N 1/3754 29/25.42 |
| 5,639,264 A | | 6/1997 | Belopolsky et al. |
| 5,650,759 A | | 7/1997 | Hittman et al. |
| 5,735,884 A | | 4/1998 | Thompson et al. |
| 5,783,772 A | * | 7/1998 | Takahashi ............ H05K 9/0018 174/152 R |
| 5,896,267 A | | 4/1999 | Hittman et al. |
| 6,765,779 B2 | | 7/2004 | Stevenson et al. |
| 7,719,854 B2 | | 5/2010 | Youker et al. |
| 7,794,256 B1 | | 9/2010 | Sochor |
| 2007/0203529 A1 | | 8/2007 | Iyer et al. |

* cited by examiner

FILTERED FEEDTHROUGH ASSEMBLY FOR IMPLANTABLE MEDICAL ELECTRONIC DEVICES

CROSS-REFERENCE TO RELATED APPLICATION

This application claims priority to Provisional Application No. 61/943,130, filed Feb. 21, 2014, which is herein incorporated by reference in its entirety.

TECHNICAL FIELD

The present disclosure relates to hermetic seal feedthroughs and electromagnetic interference filters integrated into one or more feedthrough assemblies. The present disclosure particularly relates to hermetic seal feedthroughs containing a printed circuit board (PCB) with multiple ground layers and multiple ground pins.

BACKGROUND

Medical devices may be surgically implanted within a patient and may include devices such as cardiac pacemakers, defibrillators, neurostimulators, and cardiac monitors. These implantable medical devices typically include a hermetically-sealed metal case including circuitry for generating electrical signals that are delivered to the patient's heart through one or more conductors that pass from the interior of the can to the exterior of the can through a feedthrough assembly that includes the hermetic seal. This hermetic seal serves to isolate the circuitry within the metal case from tissue, blood, and other patient fluid.

In addition to the electrical signals generated by the circuitry of the implantable medical device, externally generated electromagnetic signals can also pass through the hermetic seal via the feedthrough assembly and interfere with proper operation of the implantable medical device. Thus, electromagnetic interference filters are often integrated into implantable medical devices to filter these externally generated electromagnetic signals to maintain the intended voltage levels along the conductors. The electromagnetic filters typically include complex multilayer laminated capacitors that are configured to filter external signals of hundreds of volts and are therefore often quite expensive, which may increase the cost of the implantable medical device as a whole. Thus, there is a need for improved filtered feedthrough assemblies for implantable medical devices.

SUMMARY

In Example 1, a filtered feedthrough assembly for an implantable medical device, the filtered feedthrough assembly comprising a ferrule, an electrical insulator, a feedthrough conductor, a printed circuit board (PCB) and a capacitor. The ferrule is configured for attaching the feedthrough assembly to the implantable medical device. The electrical insulator is coupled to the ferrule by a connection element. The feedthrough conductor extends through the electrical insulator. The PCB is coupled to the ferrule or the electrical insulator, the PCB including a ground layer and a plurality of vias, the connection element being electrically coupled to the ground layer through the vias. The capacitor has a ground terminal electrically coupled to the ground layer through at least one of the vias, and a conductor terminal electrically coupled to the feedthrough conductor.

In Example 2, the filtered feedthrough assembly of Example 1, further comprising a conductive epoxy disposed within at least one of the vias to electrically couple the connection element to the ground layer.

In Example 3, the filtered feedthrough assembly of either of Examples 1 or 2, wherein the PCB includes a plurality of ground layers and wherein the vias traverse the plurality of ground layers.

In Example 4, the filtered feedthrough assembly of any of Examples 1-3, further comprising a plurality of feedthrough conductors extending through the electrical insulator, and a plurality of capacitors each associated with one of the plurality of feedthrough conductors.

In Example 5, the filtered feedthrough assembly of any of Examples 1-4, wherein each capacitor includes a ground terminal electrically coupled to the plurality of ground layers by at least one of the vias, and a conductor terminal electrically coupled to a respective one of the feedthrough conductors.

In Example 6, the filtered feedthrough assembly of any of Examples 1-5, further comprising at least one ground pin electrically coupled to the ground layers.

In Example 7, the filtered feedthrough assembly of any of Examples 1-6, wherein the number of ground pins equals the number of ground layers of the PCB.

In Example 8, the filtered feedthrough assembly of any of Examples 1-7, wherein the connection element is a gold braze material disposed so as to attach the electrical insulator to the ferrule.

In Example 9, the filtered feedthrough assembly of any of Examples 2-8, wherein the conductive epoxy is disposed within the at least one of the plurality of vias adjacent to the connection element material so as to provide a continuous electrical path between the connection element and the plurality of ground layers.

In Example 10, the filtered feedthrough assembly of Example 9, wherein the conductive epoxy is disposed within multiple vias adjacent to the connection element so as to provide a plurality of continuous electrical paths between the connection element and the plurality of ground layers.

In Example 11, the filtered feedthrough assembly of any of Examples 2-9, wherein the conductive epoxy is a silver conductive epoxy.

In Example 12, an implantable medical device comprising an implantable pulse generator including a metal case defining a hermetically-sealed inner region and an outer region, and the filtered feedthrough assembly of any of Examples 1-11. The ferrule is hermetically attached to the metal case of the implantable pulse generator such that the feedthrough conductors extend from the outer region to the inner region.

In Example 13, the implantable medical device of Example 12, further comprising an implantable lead coupled to the pulse generator and including a plurality of electrodes, each electrode electrically coupled to at least one of the feedthrough conductors.

In Example 14, a method of making a filtered feedthrough assembly for an implantable medical device, the method comprising providing a PCB having a ground layer, a plurality of vias, and at least one capacitor having a ground terminal electrically coupled to the ground layer through at least one of the vias, and a conductor terminal, and coupling an electrical insulator to a ferrule using a connection element. The method further comprises disposing a feedthrough conductor through the electrical insulator, and coupling the PCB to one or more of the ferrule, the electrical insulator and the feedthrough conductor. The method further comprises electrically coupling the feedthrough conductor and the conductor terminal of the capacitor, and electrically coupling the connection element to the ground layer through the vias.

In Example 15, the method of Example 14, wherein electrically coupling the connection element to the ground layer(s) includes injecting conductive epoxy into the vias to form a plurality of conductive paths between the connection element and the ground layer(s).

In Example 16, the method of either of Examples 14 or 15, wherein forming the PCB includes forming a PCB having a plurality of ground layers, and wherein the plurality of vias traverse the plurality of ground layers.

In Example 17, a filtered feedthrough assembly for an implantable medical device, comprising a metallic ferrule, an electrical insulator, a plurality of feedthrough conductors, a printed circuit board (PCB), and a plurality of capacitors. The metallic ferrule is configured to be hermetically attached to a metal case of the implantable medical device, and the electrical insulator is coupled to the metallic ferrule by an electrically conductive connection element. The plurality of feedthrough conductors extend through the insulator from a first side to a second side thereof. The PCB is disposed adjacent to the second side of the insulator, the PCB including a plurality of ground layers, and a plurality of vias traversing the ground layers, the vias configured to provide a plurality of electrically conductive paths through the ground layers. The plurality of capacitors each have a ground terminal and a conductor terminal, wherein the ground terminal is electrically coupled to the plurality of ground layers through at least one of the plurality of vias, and the conductor terminal is electrically coupled to at least one of the plurality of feedthrough conductors.

In Example 18, the filtered feedthrough assembly of Example 17, wherein the electrically conductive connection element is electrically coupled to the plurality of ground layers through the plurality of vias.

In Example 19, the filtered feedthrough assembly of either of Examples 17 or 18, wherein a conductive epoxy is disposed within the plurality of vias so as to electrically couple the electrically conductive connection element to the plurality of ground layers.

In Example 20, the filtered feedthrough assembly of any of Examples 17-19, wherein the electrically conductive connection element is a gold braze material disposed so as to attach the electrical insulator to the metallic ferrule, and wherein the conductive epoxy is disposed within at least one of the plurality of vias adjacent to the gold braze material so as to provide a plurality of electrical paths electrically coupling the gold braze material to the plurality of ground layers.

In Example 21, the filtered feedthrough assembly of any of Examples 17-20, further comprising at least one ground pin electrically coupled to the plurality of ground layers.

In Example 22, the filtered feedthrough assembly of Example 21, wherein the at least one ground pin is coupled to the plurality of ground layers by a conductive epoxy injected into at least one of the plurality of vias.

In Example 23, the filtered feedthrough assembly of any of Examples 17-22, wherein the plurality of ground layers comprises one of four ground layers, three ground layers, and two ground layers.

In Example 24, an implantable medical device comprising a metal case defining a hermetically-sealed inner region and an outer region, pulse generator circuitry disposed within the inner region, and a filtered feedthrough assembly. The filtered feedthrough assembly includes a metallic ferrule, an electrical insulator, a plurality of feedthrough conductors, a printed circuit board (PCB), and a plurality of capacitors. The ferrule is hermetically attached to the metal case of the implantable medical device. The electrical insulator is coupled to the metallic ferrule by an electrically conductive connection element. The plurality of feedthrough conductors extend through the insulator from the outer region to the inner region, at least some of the feedthrough conductors being operatively coupled to the pulse generator circuitry within the inner region and further being configured to be operatively coupled and to an electrode on an implantable lead. The PCB is disposed adjacent to the electrical insulator within the inner region, the PCB including a plurality of ground layers, and a plurality of vias traversing the ground layers, the vias configured to provide a plurality of electrically conductive paths through the ground layers. The plurality of capacitors each have a ground terminal and a conductor terminal, wherein the ground terminal is electrically coupled to the plurality of ground layers through at least one of the plurality of vias, and the conductor terminal is electrically coupled to at least one of the plurality of feedthrough conductors.

In Example 25, the implantable medical device of Example 24, wherein the electrically conductive connection element is electrically coupled to the plurality of ground layers through the plurality of vias.

In Example 26, the implantable medical device of either of Examples 24 or 25, wherein a conductive epoxy is disposed within at least one of the plurality of vias so as to electrically couple the electrically conductive connection element to the plurality of ground layers.

In Example 27, the implantable medical device of any of Examples 24-26, wherein the conductive epoxy is disposed within each of the plurality of vias to contact the electrically conductive connection element so as to provide a plurality of electrical paths electrically coupling the electrically conductive connection element to the plurality of ground layers.

In Example 28, the implantable medical device of any of Examples 24-27, wherein the electrically conductive connection element is a gold braze material disposed so as to attach the electrical insulator to the metallic ferrule, and wherein the conductive epoxy is disposed within each of the plurality of vias to contact the gold braze material so as to provide a plurality of electrical paths electrically coupling the gold braze material to the plurality of ground layers.

In Example 29, the implantable medical device of any of Examples 24-28, further comprising at least one ground pin electrically coupled to the plurality of ground layers.

In Example 30, the implantable medical device of Example 29, wherein the at least one ground pin is coupled to the plurality of ground layers by a conductive epoxy injected into at least one of the plurality of vias.

In Example 31, the implantable medical device of any of Examples 24-30, wherein the plurality of ground layers comprises one of four ground layers, three ground layers, and two ground layers.

In Example 32, a method of making a filtered feedthrough assembly for an implantable medical device, the method comprising providing a PCB having a plurality of ground layers, a plurality of vias extending through the ground layer, and a plurality of capacitors, each of the capacitors having a conductor terminal and a ground terminal electrically coupled to the plurality of ground layers through at least one of the vias. The method further comprises coupling an electrical insulator to a ferrule using an electrically conductive connection element, and disposing a plurality of feedthrough conductors through the electrical insulator and attaching the feedthrough conductors to the electrical insulator. In addition, the method comprises coupling the PCB to one or more of the ferrule, the electrical insulator and the feedthrough conductors, electrically coupling each of the feedthrough conductors to the conductor terminal of a respective one of the capacitors, and electrically coupling the connection element to the plurality of ground layers through the vias.

In Example 33, the method of Example 32, further comprising electrically coupling a plurality of ground pins to the ferrule of the feedthrough assembly.

In Example 34, the method of either of Examples 32 or 33, wherein electrically coupling the connection element to the plurality of ground layers includes disposing a conductive material in the plurality of vias so as to contact the connection element and provide a plurality of parallel electrical paths from the connection element to the plurality of ground layers.

In Example 35, the method of Example 34, wherein disposing the conductive material in the plurality of vias includes disposing a conductive epoxy in the plurality of vias.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
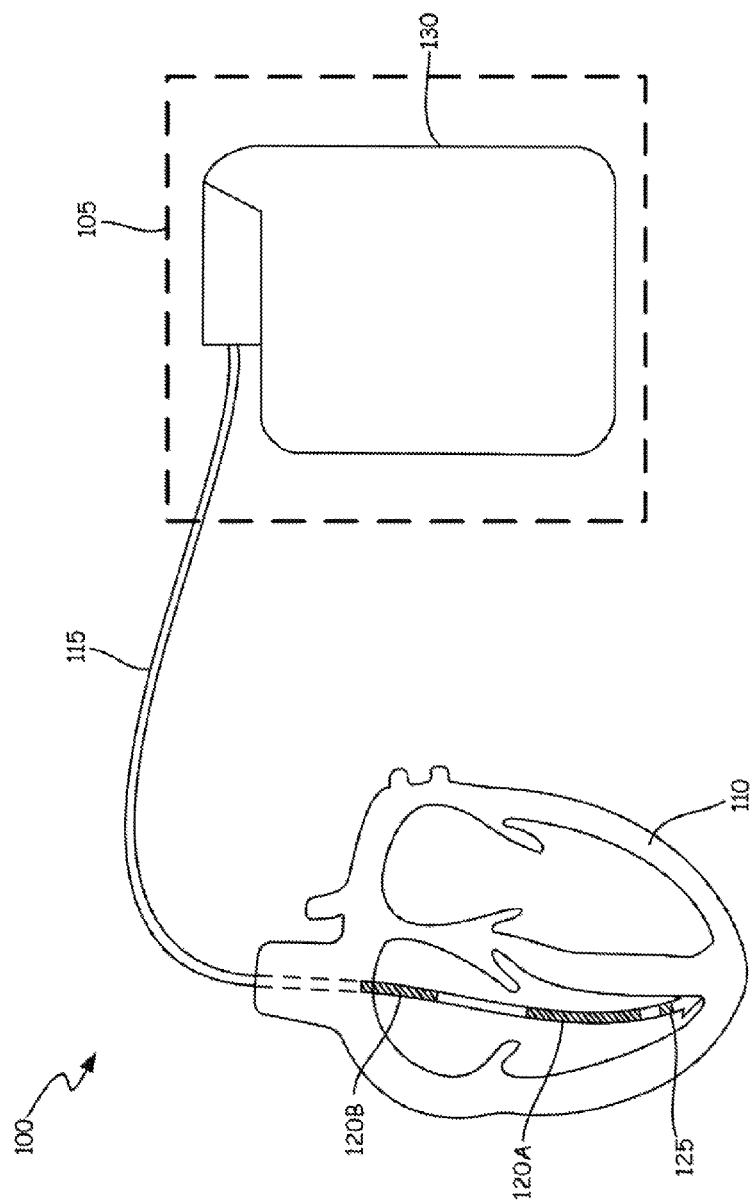
FIG. 1 is an example of an implantable medical device including a feedthrough assembly according to the present disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

In the following detailed description, reference is made to the accompanying drawings which form a part hereof, and specific embodiments in which the disclosure may be practiced are shown by way of illustration. It is to be understood that other embodiments may be used and structural changes may be made without departing from the scope of the present disclosure.

The present disclosure presents a feedthrough assembly for implantable medical devices that includes a multilayer printed circuit board with multiple ground layers that serve as a parallel-path ground return mechanism of an electromagnetic filter system of the feedthrough assembly. In addition, the feedthrough assembly may include a plurality of ground pin connections, which, along with the multiple ground layers, decrease inductive effects of the ground path, improve signal attenuation properties of the feedback assembly, and bolster the overall band filtering performance of the electromagnetic filter system.

FIG. 1 is a generalized schematic diagram of one embodiment of a system 100. The system shown is a portion of a cardiac rhythm management system. Various embodiments of system 100 include external or implantable pulse generators, pacer/defibrillators, cardioverters, defibrillators, cardiac resynchronization therapy (CRT) systems, any combination of the foregoing, or any other system using or maintaining cardiac rhythms. Further system embodiments include any implantable medical device that requires a hermetic seal, such as neuro-stimulators, insulin pumps, implantable sensors, and the like.

In the embodiment of FIG. 1, cardiac rhythm management system 100 includes an implantable pulse generator 105 coupled to heart 110 via one or more endocardial or epicardial leads, such as a lead 115. In the illustrated embodiment, the lead 115 includes one or more defibrillation electrodes, such as for delivering defibrillation therapy via first defibrillation electrode 120A and/or second defibrillation electrode 120B. As shown, the lead 115 may also include additional electrodes, such as for delivering pacing therapy via a pacing/sensing electrode 125 (which in the illustrated embodiment is configured as a ring electrode). In various embodiments, the lead 115 may also include an additional tip electrode at the distal end thereof, which in conjunction with the ring electrode 125 can provide for bi-polar pacing and sensing capabilities.

In the illustrated embodiment, the lead 115 is shown extending into the right ventricle of the heart 110. In other embodiments, additional leads can be coupled to the implantable pulse generator 105 for implantation within, for example, the right atrium and/or the coronary venous system (i.e., for pacing/sensing of the left ventricle in a bi-ventricular pacing scheme such as a CRT system).

Because the pulse generator 105 is implantable, it includes a hermetic seal for isolating the electronic components within the pulse generator from the external environment. Electrical signals sensed on the lead or leads need to pass through the hermetic seal to communicate with the electronics of the pulse generator 105 that are internal to the metal case 130. Electrical signals originating from the internal electronics for delivery to the heart 110 by the lead 115 also need to pass through the hermetic seal. The system 100 shown is a generalized system. Typically several electrical signals pass through the hermetic seal.

Figure 2A:
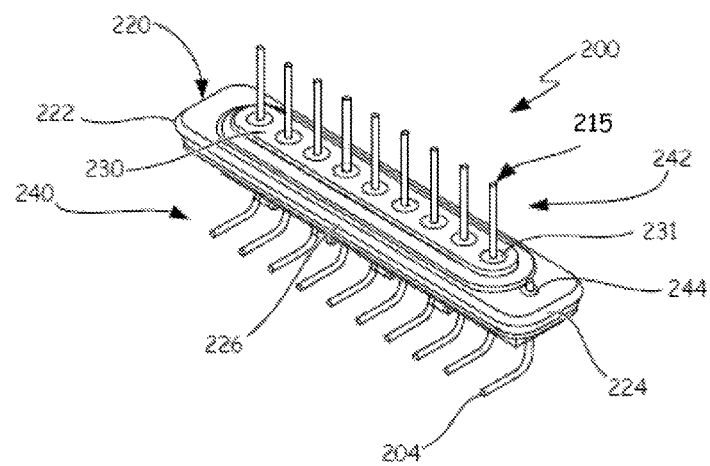
FIG. 2A is a top perspective view of an exemplary feedthrough assembly according to embodiments of the present disclosure.
Figure 2B:
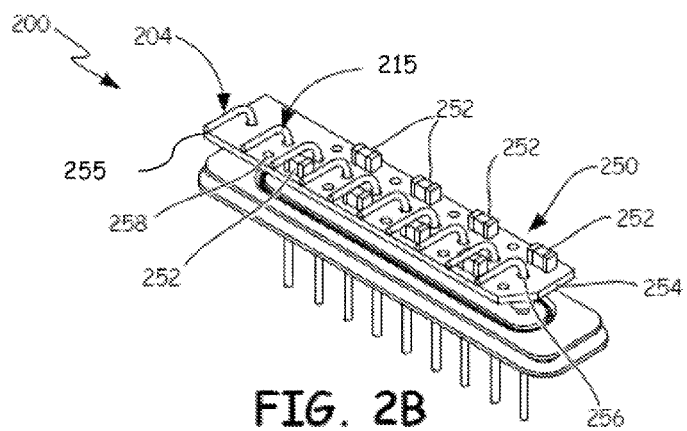
FIG. 2B is a bottom perspective view of an exemplary feedthrough assembly according to embodiments of the present disclosure.

FIGS. 2A and 2B are top and bottom perspective views, respectively, of an embodiment of a feedthrough assembly 200 for use in the implantable pulse generator 105 of FIG. 1. As shown, the feedthrough assembly 200 includes a plurality of feedthrough conductors 215 and a ferrule 220, which in the illustrated embodiment has a first end 222 and a second end 224 and a middle portion 226 between the first end 222 and the second end 224. In some embodiments, the ferrule 220 may be formed of titanium or any other metallic material. Furthermore, the ferrule 220 is configured to be coupled to the metal case 130 (see FIG. 1) of an implantable medical device by placing the ferrule 220 in an opening in the metal case 130 and welding the ferrule 220 to the metal case 130 at an outer perimeter of the ferrule 220.

As further shown, the feedthrough assembly 200 includes an electrical insulator 230, which may be mounted within or coupled to the ferrule 220, for example, using gold brazing techniques. The electrical insulator 230 may include a plurality of holes 231 through which the feedthrough conductors 215 may pass. The feedthrough conductors 215 may be mounted within and extend through the plurality of holes 231 and may extend through the respective feedthrough holes 231 so as to extend from an outer portion 242 to an inner portion 240 of the feedthrough assembly 200. The feedthrough conductors 215 may be hermetically connected to the electrical insulator 230 at the holes 231, for example, using a gold-brazed joint, soldered joint, welded joint, or other coupling method providing a hermetic connection between the feedthrough conductors 215 and the electrical insulator 230. In the various embodiments, the feedthrough conductors 215 operate to electrically couple the lead electrodes (see FIG. 1) to pulse generator circuitry within the inner region defined by the metal case 130 of the pulse generator 105. In various examples, the feedthrough conductors 215 are pins, wires (e.g., gold-plated wires, palladium alloy wires, and platinum alloy wires), or a combination thereof.

As further shown, the feedthrough assembly 200 may include a ground wire 204, which may be electrically coupled to a ground pin 244 attached to the ferrule 220. In an aspect, the ground pin 244 may be attached and electrically coupled to the ferrule 220 by welding or brazing. In some examples, the ground wire 204 and/or ground pin 244 may comprise a circuit trace, weld, brazing joint, via, electrically conductive epoxy, or any other conductive material configured to provide an electrical ground to the feedthrough assembly 200. Furthermore, though a single ground wire 204 and ground pin 244 are shown, a plurality of ground pins 244 and/or ground wires 204 may be provided in feedthrough assembly 200 to provide parallel ground paths for electromagnetic signals to be filtered. In various embodiments, the ground wire 204 and/or ground pin 244 are omitted.

As further shown in FIG. 2B, the feedthrough assembly 200 includes a plurality of capacitors 252 and a printed circuit board (PCB) 254 having a plurality of holes 256 extending therethrough. As shown, the feedthrough conductors 215 are positioned through the holes 256 of the PCB 254. The PCB 254 provides the electrical coupling between the capacitors 252 and the feedthrough conductors 215 via electrical traces (not illustrated) on the PCB that are electrically coupled to a conductor terminal (not illustrated) on each capacitor 252. As will be appreciated, the use of electrical traces to connect components on a PCB will be readily understood by the skilled artisan, and need not be discussed in greater detail herein.

In the various embodiments, except as specifically described herein, the PCB 254 can have a conventional PCB configuration, including a non-conductive substrate and conductive traces and/or pads formed thereon, including a ground layer 255 that can be electrically coupled to the metal case 130 of the implantable pulse generator 105 of FIG. 1 (through, for example, the ground wire 204 and ground pin 244, if present, or by directly attaching the ground layer 255 to the metal ferrule 220 using a conductive attachment means such as metal brazing and also attaching the ferrule 220 to the metal case 130 using a similar conductive attachment means, such as metal brazing or a weld) so as to serve as an electrical ground for the feedthrough assembly 200.

Additionally, PCB 254 includes a plurality of vias 258 extending through the PCB 254 and, consequently, the ground layer 255. In various embodiments, the surfaces of the vias 258 are plated with a conductive metal (e.g., copper, aluminum, and the like) to provide conductive paths to the ground layer 255 of the PCB 254. Additionally, the vias 258 are operable to provide an electrical ground path for the capacitors 252 by an electrical trace (not shown) electrically coupling the conductive plating of a respective via 258 to a ground terminal (not shown) on each capacitor 252.

As explained in additional detail elsewhere herein, a plurality of the vias 258 may be filled with conductive material (e.g. conductive epoxy, silver conductive epoxy, aluminum, copper, etc.) to further enable effective EMI filtering by providing multiple ground paths for elements of the feedthrough assembly 200. In particular, the vias 258 can provide multiple electrical paths to ground to the conductive connection element (e.g., gold braze material) used to attach the electrical insulator 230 to the ferrule 220.

In one embodiment, the capacitors 252 have a breakdown voltage that is configured to withstand defibrillation or electrocautery voltages that may be introduced to the feedthrough assembly 200 from the exterior through feedthrough holes 231. In some examples, the capacitors 252 have a breakdown voltage in the range of 400 volts to 2000 volts or may have a breakdown voltage of about 1500 volts. Furthermore, capacitors 252 may be ceramic capacitors and may be configured to be surface-mounted to PCB 254 and/or wire-mounted or soldered thereto. Additionally, capacitors 252 may have a capacitance value configured to filter signals having a particular frequency and/or voltage value. For example, in some embodiments, capacitors 252 may have capacitance values configured to tune the capacitors to filter signals having frequencies in a band utilized in magnetic resonance imaging processes.

Figure 3:
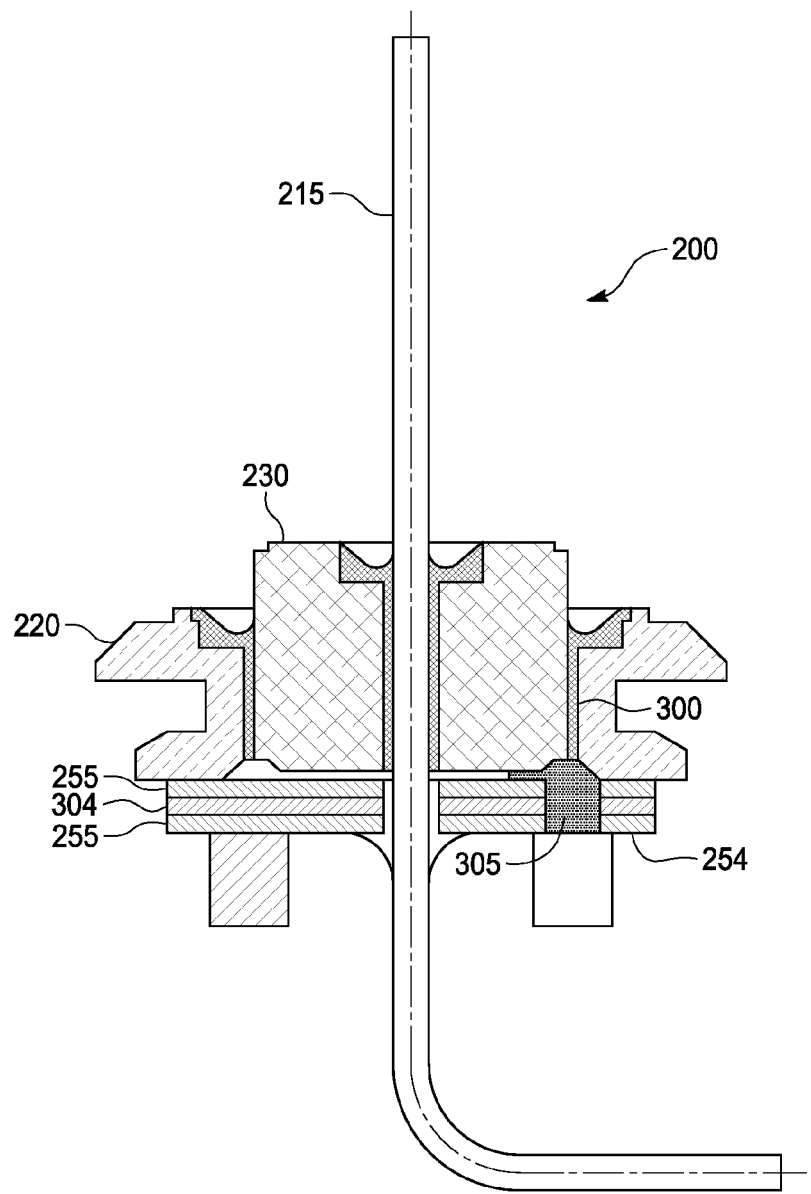
FIG. 3 is a cross-sectional elevation view through the feedthrough assembly of FIGS. 2A-2B.

FIG. 3 is a cross-sectional elevation view of the feedthrough assembly 200 according to one embodiment. As can be seen in FIG. 3, the electrical insulator 230 is attached to an inner surface of the ferrule 220 by an attachment or connection element 300. In various embodiments, the connection element 300 is made of an electrically conductive material. In various embodiments, the connection element 300 may be formed by a brazing operation using a conductive metal such as gold, silver and the like, which forms a hermetic bond between the electrical insulator 230 and the inner surface of the ferrule 220. Similarly, the feedthrough conductor 215 may also be attached to an inner surface of the electrical insulator 230 and to the PCB 254 (and consequently, the one or more ground layers 255 thereof) by the same or a similar conductive attachment technique.

FIG. 3 further illustrates one of the vias 258 disposed adjacent to an inner side of the ferrule 220 and the electrical insulator 230 (i.e., the side corresponding to the hermetically-sealed inner region of the implantable pulse generator 105 enclosed by the metal case 130, see FIG. 1). As further shown, a conductive material 305 is disposed within the via 258 so as to contact the connection element 300 to provide an electrical path through the PCB 254. Furthermore, because the via 258 extends through the ground layer 255 of the PCB 254, the conductive material 305 also provides an electrically conductive path to electrically couple the connection element 300 to the ground layer 255. In various embodiments, a plurality of the vias 258 are also disposed in the same manner as the via 258 illustrated in FIG. 3 (i.e., adjacent to the inner surface of the electrical insulator 230), and are also filled with the conductive material 305 in the same or a similar manner so as to form multiple conductive paths between the connection element 300 and the ground layer 255.

In various embodiments, the conductive material 305 may be any conductive material capable of being disposed into the one or more vias 258. In one embodiment, the conductive material 305 is a conductive epoxy, e.g., a silver conductive epoxy, a conductive polymer, or a metallic material such as copper.

In various embodiments, the PCB 254 may be a multi-layer PCB including a plurality of ground layers separated by suitable insulating layers 304. In such embodiments, the vias 258 can extend through the entire thickness of the multi-layer PCB, thus providing an electrical connection to the multiple ground layers. In various embodiments, the multi-layer PCB 254 can have three ground layers and four insulating layers, though any number of ground layers 255 or insulating layers 304 are contemplated by the present disclosure. Additionally, in some embodiments utilizing one or more ground pins 244 (see FIGS. 2A-2B), the PCB 254 may include the same number of ground pins as the number of ground layers in the PCB 254.

In some embodiments, multilayer PCB 254 may comprise a multilayer FR4 PCB. Insulating layers may comprise any electrical insulating material or dielectric, such as, but not limited to FR4, glass epoxy, silicates, or the like. Additionally, the ground layers of multilayer PCB 254 may comprise layers of conductive material, which may include any conductive material, such as, but not limited to copper, aluminum, or any other conductive metal or semiconductor. In some embodiments, one or more layers of copper or aluminum foil may be laminated to one or both sides of an insulating material (e.g., FR4 material) to form alternating ground and insulating layers.

Figure 4:
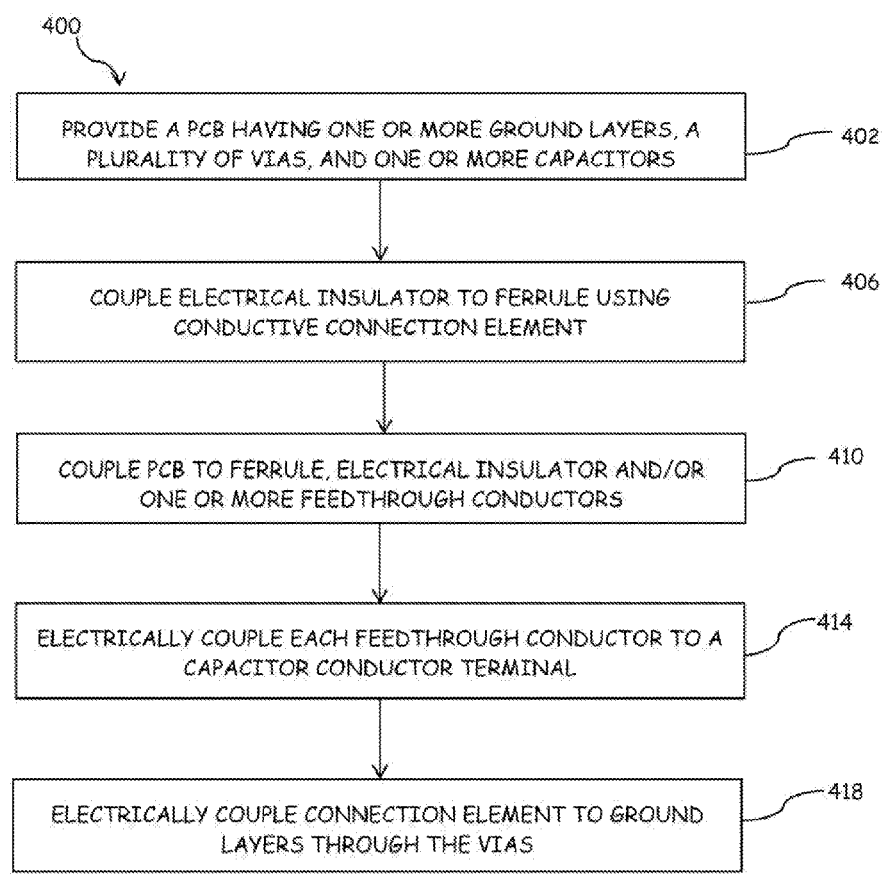
FIG. 4 is an example method of forming a feedthrough assembly according to example embodiments of the present disclosure.

FIG. 4 is a flow diagram of an example method 400 of providing a feedthrough assembly for filtering electromagnetic interference in an implantable medical device. Method 400 is provided as a set of steps represented by blocks. Though the various steps are presented in a particular order in example method 400 as illustrated in FIG. 4, it is to be understood that one or more of these steps may be performed in a different order than illustrated and/or may be excluded from the example method without departing from the methods contemplated herein.

For example, at block 402, method 400 may include providing a PCB having one or more ground layers, a plurality of vias extending through the ground layers, and one or more capacitors. In one embodiment, providing the PCB can include forming a plurality of ground layers and at least one insulating layer in a multilayer PCB. In some examples, this may include forming the ground layers and insulating layers by deposition, etching, photolithography, FR4 circuit layer bonding, or any other method of forming layers of conductors and insulators in a multilayer PCB.

Furthermore, at block 406, the method 400 may include coupling an electrical insulator to a feedthrough ferrule using a conductive connection element. In one embodiment, the electrical insulator may be soldered or brazed to the ferrule using a conductive metal such as gold or silver as the soldering or brazing metal.

In an additional aspect, method 400 may include, at block 410, coupling the PCB to the ferrule, the electrical insulator, and/or one or more feedthrough conductors disposed through the electrical insulator. In one embodiment, the feedthrough conductors are also attached to the electrical insulator and/or the PCB using an electrically conductive material such as a metal braze material (e.g., gold). In addition, the method 400 further includes, at block 414, electrically coupling each feedthrough conductor to a conductor terminal on a respective one of the capacitors. In various embodiments, a ground terminal on each capacitor is electrically connected, e.g., via solder to a trace on the PCB, to one of the vias (which is plated with a conductive material) so as to electrically couple the respective ground terminal to the ground layers of the PCB.

At block 418, the method 400 further includes electrically coupling the connection element to the ground layer(s) of the PCB through the vias. In one embodiment, a conductive material is disposed in the plurality of vias, and this conductive material contacts the connection element to provide a plurality of electrical paths from the connection element to the ground layers. In various embodiments, the conductive material may be a conductive epoxy, conductive polymer, metal, and the like.

In addition, in some examples, method 400 may include electrically coupling the plurality of ground layers to one or more ground pins, which can be electrically coupled to the ferrule of the feedthrough assembly. Furthermore, the method 400 may include securing the feedthrough assembly to a metal can of the implantable medical device.

Various modifications and additions can be made to the exemplary embodiments discussed without departing from the scope of the present disclosure. For example, while the embodiments described herein refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A filtered feedthrough assembly for an implantable medical device, comprising:
   a ferrule configured to be attached to a metal case of the implantable medical device;
   an electrical insulator coupled to the ferrule by a connection element;
   a feedthrough conductor extending through the electrical insulator;
   a printed circuit board (PCB) coupled to at least one of the ferrule and the electrical insulator, the PCB including a ground layer and a plurality of vias, the connection element being electrically coupled to the ground layer through the vias; and
   a capacitor having a ground terminal electrically coupled to the ground layer through at least one of the vias, and a conductor terminal electrically coupled to the feedthrough conductor.

2. The filtered feedthrough assembly of claim 1, further comprising a conductive epoxy disposed within at least one of the vias to electrically couple the connection element to the ground layer.

3. The filtered feedthrough assembly of claim 1, wherein the PCB includes a plurality of ground layers and wherein the vias traverse the plurality of ground layers.

4. The filtered feedthrough assembly of claim 3, further comprising a plurality of feedthrough conductors extending through the electrical insulator, and a plurality of capacitors each associated with one of the plurality of feedthrough conductors.

5. The filtered feedthrough assembly of claim 4, wherein each capacitor of the plurality of capacitors includes a ground terminal electrically coupled to the plurality of ground layers by at least one of the vias, and a conductor terminal electrically coupled to a respective one of the feedthrough conductors.

6. The filtered feedthrough assembly of claim 3, further comprising at least one ground pin electrically coupled to the ground layers.

7. The filtered feedthrough assembly of claim 6, wherein the number of ground pins equals the number of ground layers of the PCB.

8. The filtered feedthrough assembly of claim 1, wherein the connection element is a gold braze material disposed so as to attach the electrical insulator to the ferrule.

9. The filtered feedthrough assembly of claim 1, wherein a conductive epoxy is disposed within at least one of the plurality of vias to contact the connection element so as to provide a continuous electrical path between the connection element and the ground layer.

10. A filtered feedthrough assembly for an implantable medical device, comprising:
 a ferrule configured to be attached to a metal case of the implantable medical device;
 an electrical insulator coupled to the ferrule by an electrically conductive connection element;
 a plurality of feedthrough conductors extending through the electrical insulator from a first side to a second side thereof;
 a printed circuit board (PCB) disposed adjacent to the second side of the electrical insulator, the PCB including a plurality of ground layers, and a plurality of vias traversing the ground layers, the vias configured to provide a plurality of electrically conductive paths through the ground layers, wherein the electrically conductive connection element is electrically coupled to the plurality of ground layers through the plurality of vias; and
 a plurality of capacitors each having a ground terminal and a conductor terminal, wherein the ground terminal is electrically coupled to the plurality of ground layers through at least one of the plurality of vias, and the conductor terminal is electrically coupled to at least one of the plurality of feedthrough conductors.

11. The filtered feedthrough assembly of claim 10, wherein a conductive epoxy is disposed within the plurality of vias so as to electrically couple the electrically conductive connection element to the plurality of ground layers.

12. The filtered feedthrough assembly of claim 11, wherein the electrically conductive connection element is a gold braze material disposed so as to attach the electrical insulator to the ferrule, and wherein the conductive epoxy is disposed within at least one of the plurality of vias to contact the gold braze material so as to provide a plurality of electrical paths electrically coupling the gold braze material to the plurality of ground layers.

13. The filtered feedthrough assembly of claim 10, further comprising at least one ground pin electrically coupled to the plurality of ground layers.

14. The filtered feedthrough assembly of claim 13, wherein the at least one ground pin is coupled to the plurality of ground layers by a conductive epoxy injected into at least one of the plurality of vias.

15. The filtered feedthrough assembly of claim 10, wherein the plurality of ground layers comprises one of four ground layers, three ground layers, and two ground layers.

16. A method of making a filtered feedthrough assembly for an implantable medical device, the method comprising:
 providing a PCB having a plurality of ground layers, a plurality of vias extending through the ground layer, and a plurality of capacitors, each of the capacitors having a conductor terminal and a ground terminal electrically coupled to the plurality of ground layers through at least one of the vias;
 coupling an electrical insulator to a ferrule using an electrically conductive connection element;
 disposing a plurality of feedthrough conductors through the electrical insulator and attaching the feedthrough conductors to the electrical insulator;
 coupling the PCB to one or more of the ferrule, the electrical insulator, and the feedthrough conductors;
 electrically coupling each of the feedthrough conductors to the conductor terminal of a respective one of the capacitors; and
 electrically coupling the connection element to the plurality of ground layers through the vias.

17. The method of claim 16, further comprising electrically coupling a plurality of ground pins to the ferrule of the feedthrough assembly.

18. The method of claim 16, wherein electrically coupling the connection element to the plurality of ground layers includes disposing a conductive material in the plurality of vias so as to contact the connection element and provide a plurality of parallel electrical paths from the connection element to the plurality of ground layers.

19. The method of claim 18, wherein disposing the conductive material in the plurality of vias includes disposing a conductive epoxy in the plurality of vias.

* * * * *